US00PP27627P2

(12) United States Plant Patent
Zaiger et al.

(10) Patent No.: US PP27,627 P2
(45) Date of Patent: Jan. 31, 2017

(54) NECTARINE TREE NAMED 'POLAR GEM'

(50) Latin Name: ***Prunus persica* var. *nucipersica***
Varietal Denomination: Polar Gem

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 18 days.

(21) Appl. No.: 14/756,156

(22) Filed: Aug. 10, 2015

(51) Int. Cl.
*A01H 5/08* (2006.01)

(52) U.S. Cl.
USPC ..... Plt./188

(58) Field of Classification Search
USPC ..... Plt./188
See application file for complete search history.

*Primary Examiner* — June Hwu

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Fruit with a high degree of red skin color.
3. Heavy and regular production of large size fruit.
4. Fruit with very good flavor and eating quality.
5. Mild, sweet, sub-acid white flesh fruit.

1 Drawing Sheet

Botanical designation: *Prunus persica* var. *nucipersica*.
Variety denomination: 'Polar Gem'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

Prior Varieties

Among the existing varieties of nectarine trees, which are known to us, and mentioned herein, 'Arctic Star' Nectarine (U.S. Plant Pat. No. 9,332), 'Arctic Sweet' Nectarine (U.S. Plant Pat. No. 9,542), our proprietary non-patented nectarine seedling selections '63MA524', '54Z380', '60Z643', '237LC83' and '6LG456'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, Calif. as an open pollinated seedling selection from our proprietary non-patented nectarine seedling selection '63MA524'. The seed parent originated from a first generation cross between '54Z380' nectarine (non-patented) and '60Z643' (non-patented). '54Z380' originated from a cross between 'Arctic Star' Nectarine (U.S. Plant Pat. No. 9,332) and 'Arctic Sweet' Nectarine (U.S. Plant Pat. No. 9,542). '60Z643' originated from a cross between '237LC83' nectarine (non-patented) and '6LG456' nectarine (non-patented). A large group of these-open pollinated seedlings were budded onto older established trees of 'Nemaguard' Rootstock (non-patented) to enhance earlier fruit production for evaluation. Under close and careful observation we recognized the desirable fruit and tree characteristics of the present new variety and selected it in 2006 for a further asexual propagation and commercialization.

ASEXUAL REPRODUCTION OF THE VARIETY

In 2006 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a regular and productive bearer of large size, firm, clingstone fruit. The fruit is further characterized by having mild, sweet, sub-acid, white flesh with very good flavor and eating quality. In comparison to its seed parent (63MA524) the fruit of the new variety is larger in size and the fruit is approximately 5 days later in maturity. In comparison to the commercial variety 'Arctic Sweet' Nectarine (U.S. Plant Pat. No. 9,542) the tree of the new variety has a lower chilling requirement of approximately 150 hours at or below 45° F. and the fruit is approximately 5 days later in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 9 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height and width the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 8 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 650 hours at or below 45° F.

Trunk:

*Size*.—Large, average circumference 66.1 cm at 20.3 cm above ground on a 9 year old tree.

*Stocky*.—Medium stocky.

*Texture*.—Medium shaggy, roughness increases with age.

*Color*.—Varies from 10YR 4/2 to 10YR 2/2.

Branches:

*Size*.—Medium. Average circumference 18.1 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 24 in a 25.8 square cm section. Average length 5.9 mm. Average width 2.4 mm. Color varies from 5YR 6/8 to 5YR 4/8.

*Color*.—New growth varies from 5GY 7/6 to 5GY 7/8. Mature growth varies from 7.5YR 3/6 to 7.5YR 2/4, varies with age of growth.

Leaves:

*Size*.—Medium to large. Average length 121.8 mm. Average width 36.0 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.5 mm. Average width 1.6 mm. Longitudinally grooved. Surface glabrous. Color varies from 5GY 8/4 to 5GY 7/4.

*Glands*.—Type — reniform. Size — medium to large. Average length 1.4 mm. Average width 0.8 mm. Number varies from 1 to 3, average number 2. Located primarily on the base of the leaf blade and the upper portion of the petiole.

*Stipules*.—None present.

*Color*.—Upper surface varies from 5GY 4/4 to 5GY 3/4. Lower surface varies from 5GY 6/4 to 5GY 5/4. Midvein color varies from 5GY 8/4 to 5GY 7/4.

Flower buds:

*Size*.—Large. Average length 17.2 mm. Average diameter 10.2 mm.

*Hardiness*.—Hardy with respect to California winters.

*Density*.—Medium.

*Form*.—Plump, conical, becoming elongated before opening.

*Pedicel*.—Average length 3.9 mm. Average width 1.4 mm. Color varies from 2.5GY 6/6 to 5GY 6/6. Surface glabrous.

*Color*.—Varies from 5RP 8/6 to 7.5RP 6/10.

Flowers:

*Blooming period*.—Date of First Bloom Feb. 8, 2015. Date of Petal Fall Feb. 18, 2015, varies slightly with climatic conditions.

*Size*.—Large, showy. Average height 20.9 mm. Average diameter 44.2 mm.

*Petals*.—Number — normally 5, alternately arranged to sepals. Size — large. Average length 21.3 mm. Average width 20.8 mm. Form — orbicular. Apex — rounded. Petal base — truncated. Margin — sinuate. Arrangement — overlapping. Both upper and lower surface glabrous. Color varies from 5RP 9/2 to 5RP 8/4.

*Sepals*.—Number — normally 5, alternately arranged to petals. Size — large. Average. length 6.7 mm. Average width 5.9 mm. Shape — ovate. Apex — rounded. Margin — entire. Color — upper surface varies from 5GY 5/8 to 7.5R 3/8. Lower surface varies from 7.5R 3/4 to 7.5R 2/4. Upper surface glabrous, lower surface pubescent.

*Stamens*.—Average number per flower 48. Average filament length 13.9 mm. Filament color varies from N 9.5/(white) to 5RP 9/8. Anther color varies from 5Y 8/8 to 7.5R 3/10. On average the stamens are below the height of the petals.

*Pollen*.—Self fertile. Color varies from 5Y 8/10 to 5Y 7/12.

*Pistil*.—Normally 1. Average length 18.4 mm. Surface — glabrous. Stigma height an average of 1.5 mm below anthers. Color varies from 10Y 8.5/6 to 2.5GY 7/6.

*Fragrance*.—Moderate.

*Color*.—Varies from 5RP 9/2 to 5RP 8/4.

*Pedicel*.—Average length 4.5 mm. Average width 1.7 mm. Color varies from 2.5GY 6/8 to 5GY 6/6. Surface — glabrous.

*Number flowers per flower bud*.—Normally one.

Fruit:

*Maturity when described*.—Firm ripe and ready for consumption.

*Date of first picking*.—Jun. 18, 2015.

*Date of last picking*.—Jun. 28, 2015, varies slightly with climatic conditions.

*Size*.—Large. Average diameter axially 72.4 mm. Average transversely in suture plane 76.2 mm. Average weight 252.8 grams, varies slightly with fertility of the soil, amount of thinning and climatic conditions.

*Form*.—Globose.

*Suture*.—Slightly lipped, some fruit with slight suture.

*Ventral surface*.—Slightly lipped.

*Apex*.—Slightly retuse.

*Base*.—Flat.

*Stem cavity*.—Rounded to slightly elongated in suture plane. Average depth 13.2 mm. Average diameter 8.1 mm.

Stem:

*Size*.—Medium. Average length 9.3 mm. Average diameter 3.3 mm.

*Color*.—Varies from 10Y 6/6 to 2.5GY 6/8.

Flesh:

*Ripens*.—Evenly.

*Texture*.—Firm, meaty, crisp.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, mild, sweet, sub-acid.

*Juice*.—Heavy amount, enhances flavor.

*Acidity*.—Not available.

*Brix*.—Average Brix 16.0°, varies slightly with amount of fruit per tree and climatic conditions.

*Pit cavity*.—Average length 41.7 mm. Average width 29.4 mm. Average depth 12.3 mm. Color varies from 2.5GY 8/4 to 7.5R 3/10.

*Color*.—Varies from 10Y 9/2 to 2.5GY 9/2.

Skin:

*Thickness*.—Medium.

*Surface*.—Smooth.

*Pubescence*.—Wanting.

*Tendency to crack*.—None.

*Color*.—Ground color varies from 7.5Y 9/2 to 10Y 9/2. Overspread with 7.5R 3/10 to 7.5R 2/6.

*Tenacity*.—Tenacious to flesh.

*Astringency*.—Undetected.

Stone:

*Type*.—Clingstone, strong adherence to flesh.

*Size*.—Large. Average length 40.7 mm. Average width 28.4 mm. Average thickness 22.5 mm.

*Form*.—Obovoid.

*Base*.—Flat.

*Apex*.—Pointed. Average length 1.2 mm.

*Surface*.—Pitted throughout, pits vary from rounded to elongated.

*Sides*.—Unequal, one side extending further from suture plane.

*Ridges*.—Relatively smooth, extending from base to apex.

*Tendency to split*.—None.

*Color*.—Varies from 5YR 5/6 to 7.5YR 5/6 when dry.

Kernel:

*Size*.—Large. Average length 21.0 mm. Average width 12.8 mm. Average depth 6.2 mm.

*Form*.—Ovate.

*Viability*.—Viable, complete embryo development.

*Skin color*.—Varies from 5Y 9/4 to 7.5Y 9/4.

Use: Dessert.

*Market*.—Local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

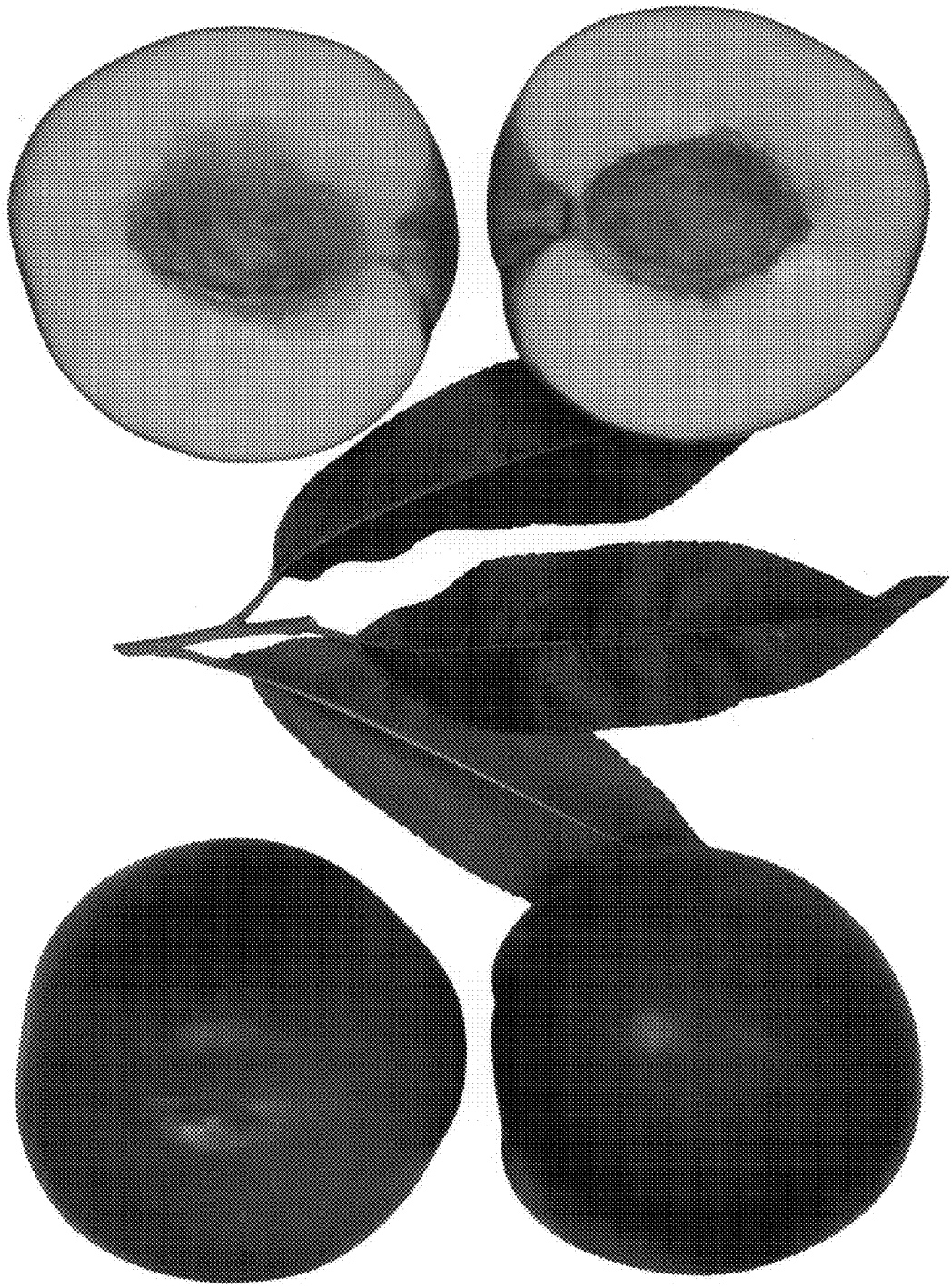

* * * * *